United States Patent
Philippe

(10) Patent No.: US 9,767,253 B2
(45) Date of Patent: Sep. 19, 2017

(54) SYSTEM AND METHOD FOR ADDING AND TRACKING PRODUCT INFORMATION TO A PATIENT RECORD

(75) Inventor: Richard Philippe, Laval (CA)

(73) Assignee: LOGI-D INC., Montreal, Quebec (CA)

( * ) Notice: Subject to any disclaimer, the term of this patent is extended or adjusted under 35 U.S.C. 154(b) by 48 days.

(21) Appl. No.: 12/428,095

(22) Filed: Apr. 22, 2009

(65) Prior Publication Data

US 2010/0274585 A1    Oct. 28, 2010

(51) Int. Cl.
G06Q 10/10 (2012.01)
G06F 19/00 (2011.01)
G06Q 50/22 (2012.01)
G06Q 50/24 (2012.01)

(52) U.S. Cl.
CPC .......... *G06F 19/322* (2013.01); *G06F 19/326* (2013.01); *G06Q 10/10* (2013.01); *G06Q 50/22* (2013.01); *G06Q 50/24* (2013.01)

(58) Field of Classification Search
USPC ......................................................... 705/2–3
See application file for complete search history.

(56) References Cited

U.S. PATENT DOCUMENTS

| | | | | |
|---|---|---|---|---|
| 5,799,981 A * | 9/1998 | Tung | ...................... | B42D 15/00 283/101 |
| 6,493,724 B1 * | 12/2002 | Cusack | ................. | G06F 19/366 |
| 6,861,954 B2 * | 3/2005 | Levin | ......................... | 340/572.1 |
| 7,080,777 B2 | 7/2006 | Wagner et al. | | |
| 7,165,721 B2 | 1/2007 | Wagner et al. | | |
| 7,454,358 B2 * | 11/2008 | Mallett | ................... | B07C 7/005 206/366 |
| 2002/0032435 A1 * | 3/2002 | Levin | ............................... | 606/1 |
| 2002/0032582 A1 * | 3/2002 | Feeney, Jr. | .......... | G06F 19/3462 705/2 |
| 2002/0143320 A1 * | 10/2002 | Levin | ..................... | A61F 13/44 606/1 |
| 2004/0199401 A1 | 10/2004 | Wagner et al. | | |
| 2004/0199545 A1 | 10/2004 | Wagner et al. | | |
| 2009/0267765 A1 * | 10/2009 | Greene | ................ | G06K 7/0008 340/568.1 |

FOREIGN PATENT DOCUMENTS

WO    WO 2008043921 A2 *   4/2008

OTHER PUBLICATIONS

Saar, et al., "Towards intelligent recycling: a proposal to link bar codes to recycling information", Resources, Conservation and Recycling 41 (2004) 15-22.*

* cited by examiner

*Primary Examiner* — Amber A Misiaszek
(74) *Attorney, Agent, or Firm* — Bereskin & Parr LLP

(57) ABSTRACT

The present system and the method relate to adding product information to patient record. A product database stores the product information corresponding to a product, while a patient database stores the patient record corresponding to a patient. A product detector detects a product identifier corresponding to the product information and generates a product identifier message. The patient detector detects a patient identifier corresponding to the patient record and generates a patient identifier message. An adding module adds the product information to the patient record based on the patient identifier message and the product identifier message.

15 Claims, 7 Drawing Sheets

SYSTEM AND METHOD FOR ADDING AND TRACKING PRODUCT INFORMATION TO A PATIENT RECORD

FIELD OF THE INVENTION

The present system and method relate to a system and method for adding product information to a patient record. More particularly, the system and method further relates to product tracking and replenishing purposes.

BACKGROUND OF THE INVENTION

Today's health care facilities include a wide range of establishments, from small and relatively simple medical clinics to large and complex hospitals. All together, health care facilities use a large amount of products for treating patients having various health conditions. In some instances, it is required to keep track of products that have been used for treatment, or installed within patients, to ensure compatibility or to readily be able to contact patients for product recalls. More particularly, in large hospitals, keeping track of such products that have been used on or installed within patients is a challenge, as it is performed manually, requires filling in multiple forms and is thus time consuming and requires a certain discipline from the part of both practitioners and personnel.

Efficient ways of monitoring product usage in health care facilities have been disclosed for product replenishment purposes. In Canadian application 2,587,186, there is disclosed a system and method for automatically alerting hospital supply personnel when the amount left of a given individually packed product is below a threshold. According to an aspect, each individually packed product has an identification label affixed to its package, as the product is used, the package is discarded into a garbage bin that is equipped with a label scanner. When the package of the product is scanned, the bin is adapted to transmit to a central server data indicative of the product's identification label. The central server then, according to the transmitted data, calculates and updates a database with the number of packed products that are left over. When the number of the particular packed product drops below a product specific threshold, the central server transmits an alert to a designated supply personnel for him to take action at replenishing the supply of the particular product that is about to run out.

However, prior art systems for monitoring products in health care facilities do not allow the automatic tracking of products that have been used for treatment or inserted within a patient in particular.

SUMMARY OF THE INVENTION

In accordance with an aspect of the present invention, there is provided a system for adding product information to a patient record. The system comprises a product database, a patient database, a product detector, a patient detector and an adding module. The product database stores the product information corresponding to a product. The patient database stores the patient record corresponding to a patient or a link to a patient record. The product detector detects a product identifier corresponding to the product information and generates a product identifier message. The patient detector detects a patient identifier corresponding to the patient record and generates a patient identifier message. Upon receipt of the patient identifier message and the product identifier message, the adding module adds the product information to the patient record.

In accordance with another aspect of the present invention, there is provided a method for adding product information to a patient record. The method inserts into a product database the product information corresponding to a product, and inserts into a patient database the patient record corresponding to a patient. Then, a product identifier corresponding to the product information is detected and a product identifier message is generated. A patient identifier corresponding to the patient record is also detected, and a patient identifier message is generated. Upon receipt of the product identifier message and the patient identifier message, the product information is added to the patient record.

BRIEF DESCRIPTION OF THE DRAWINGS

For a better understanding of aspects of the system and method described herein, and to show more clearly how they may be carried into effect, reference will be made to the accompanying drawings in which.

DETAILED DESCRIPTION OF THE INVENTION

The present relates to a system and method for adding product information to a patient record. More particularly, the present relates to adding product information to a patient record for tracking purposes in a medical environment. Although the singular form is used throughout the present specification and claims, it should be clear to those skilled in the art that in the medical environment, multiple products and patient records are concurrently respectively used and maintained, and that the present system and method are not limited to the adding of one product information to one patient record, but rather the adding of product information to patient record in general.

Figure 1:
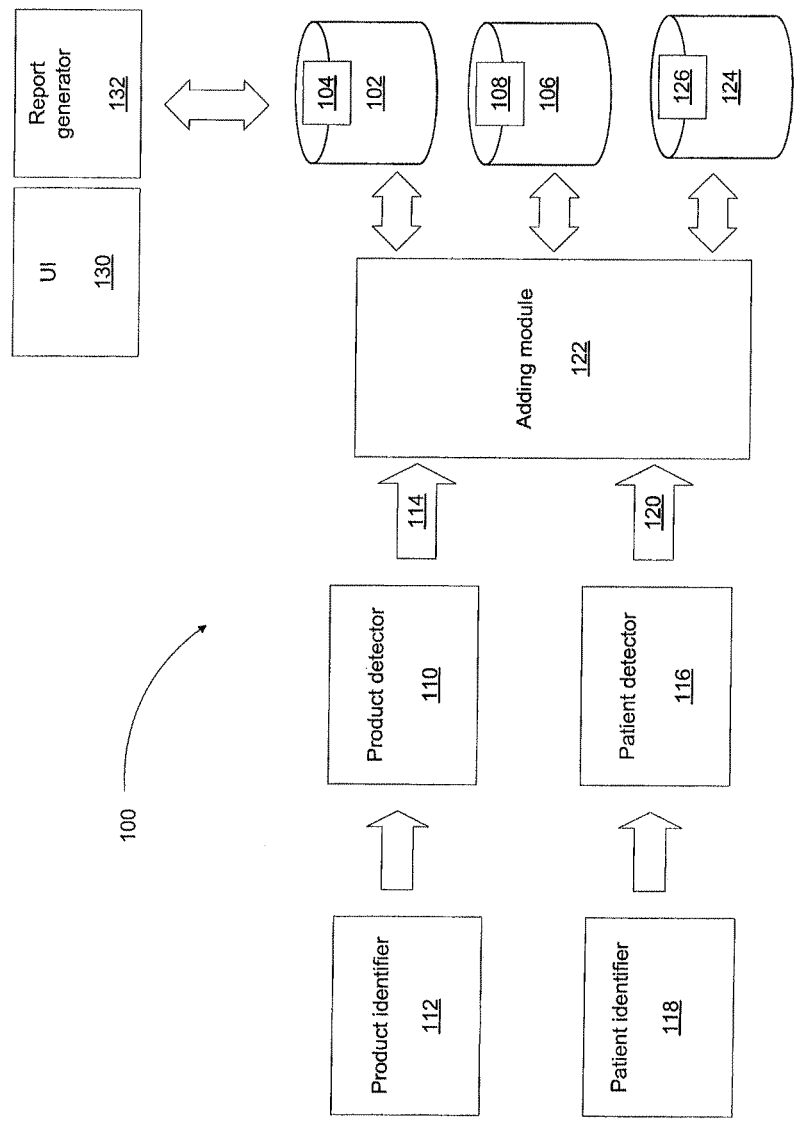
FIG. 1 is a block diagram of the system for adding a product information to a patient record.

Presented in FIG. 1 is a system 100 for adding product information to a patient record, the system 100 comprises a product database 102 for storing product information 104 for a product. To be specific, the product may correspond to one or many of a wide range of medical products such as medical implants, medical prostheses, medical substances or any other type of medical products used for treating, reconstructing or preventing a medical condition from occurring. The product information 104 may be stored in the product database 102 for example before the product is shelved for use, or when the product is received by a hospital. The system 100 further comprises a patient database 106 for storing a patient record 108 or a link to a hospital database. The patient record 108 corresponds to a description of an individual patient that is registered at a hospital. Usually, the patient record 108 holds entries that are given by the patient at patient registration. The product database 102 and the patient database 106 may be separate databases as depicted on FIG. 1, or may be incorporated into one single database holding both the product information 104 the patient record 108.

As further presented in FIG. 1, the system 100 comprises a product detector 110 for detecting a product identifier 112. More precisely, the product identifier 112 corresponds to the product information 104 stored in the product database 102. As the product identifier 112 is placed in proximity with the product detector 110, the product detector 110 detects the product identifier 112 and generates a corresponding product identifier message 114. The product identifier 112 may be any type of electronically, optically or electromagnetically detectable identifier, such as for example a bar code label, a Radio Frequency Identifier, a microchip, etc. The product identifier 112 may be affixed to a product, or to a product container or on a product package.

Similarly, the system 100 comprises a patient detector 116 for detecting a patient identifier 118. More precisely, the patient identifier 118 corresponds to the patient record 108. The patient detector 116 detects the patient identifier 118 when the patient identifier is placed in proximity with the patient detector 116. Once the patient identifier 118 is detected, the patient detector 116 generates a corresponding patient identifier message 120. The patient identifier 118 may be any type of electronically or optically detectable identifier, such as for example a bar code label, a Radio Frequency tag, a microchip, etc. The patient identifier may be affixed to the patient, affixed to a patient board, to a patient's bed, to a patient's bracelet, or to any other surface corresponding to or on the patient.

The system 100 of FIG. 1 further comprises an adding module 122. The adding module 122 is adapted to receive either directly or ultimately the product identifier message 114 and the patient identifier message 120. Upon receipt of the product identifier message 114 and the patient identifier message 120, the adding module 122 adds the product information 104 to the patient record 108. According to one aspect, the adding module 122 is electronically or wirelessly connected to both the product detector 110 and the patient detector 116, and receives from them, respectively, the product identifier message 114 and the patient identifier message 120. Based on the received messages 114, 120, the adding module 122 is adapted to add the corresponding product information 104 to the corresponding patient record 108. For doing this, in one aspect, the adding module 122 is adapted to store the product information 104 in the patient record 108. In another aspect, the adding module 122 is adapted to store the patient record 108 in the product information 104. In yet another aspect, the adding module 122 is adapted to store in a linking database 124 a link 126 that corresponds to the product information 104 and the patient record 108. In yet another aspect, instead of storing the product information 104 in the patient record 108 or vice versa, a software pointer may be used to link directly the product information 104 and the patient record 108.

According to one aspect of the system 100, the databases (102, 106 and 124) are located in a central server that is adapted to connect to a local network of the hospital. When the adding module 122 is also connected to the local network, it is possible for the adding module 122 to access the databases (102, 106 and 124) by connecting to the central server. Consequently, it is possible for multiple adding modules 122 to access the same databases (102, 106 and 124) simultaneously, when multiple patients receive medical care at the same time. Moreover, there is no need for the adding module 122 to make a database selection according to the product information 104 or to the patient record 108. Since all databases (102, 106 and 124) are centralized, each product information 104 is stored in the same product database 102 and each patient record 108 is stored in the same patient database 106.

It will be understood by a skilled reader that it is possible for the linking database 124 and the patient database 106 to be implemented as one single database and that it is also possible for the linking database 124 and the product database 102 to be implemented as one single database.

Figure 2:
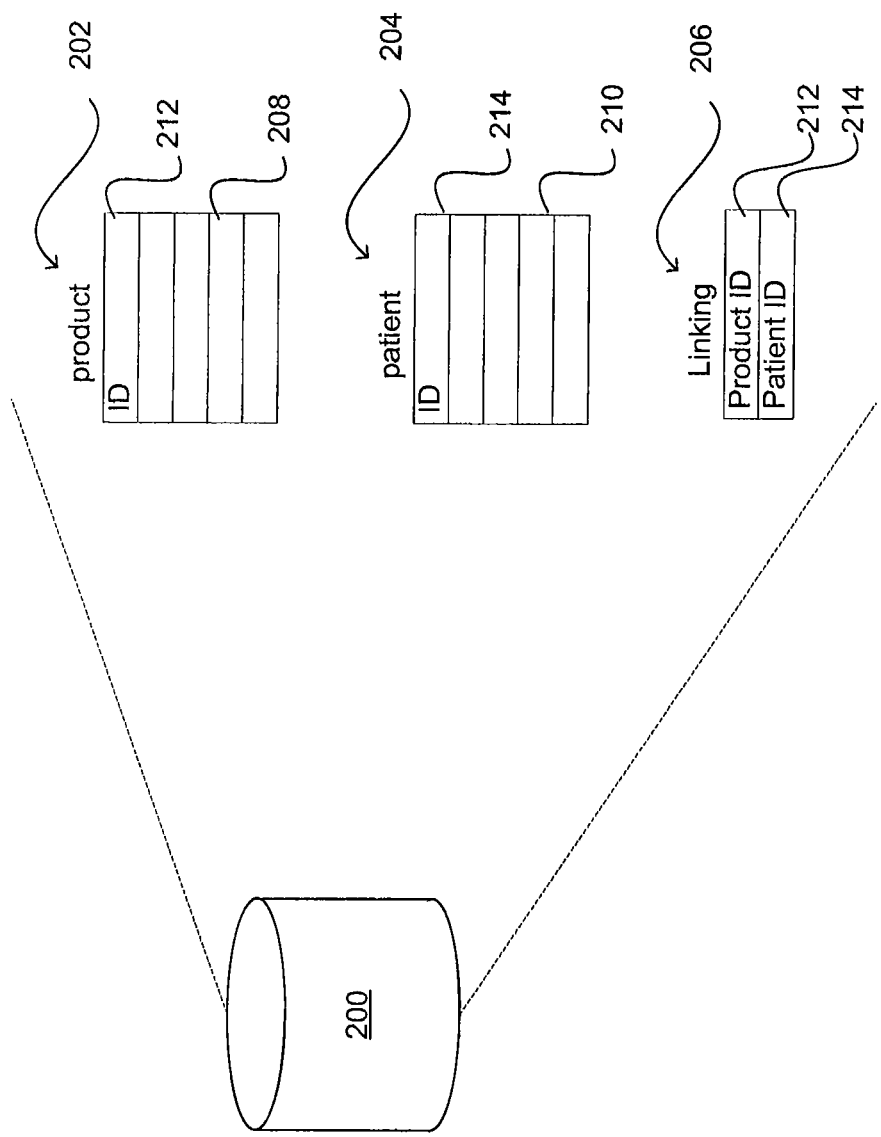
FIG. 2 is an exemplary database diagram.

Presented in FIG. 2, according to another aspect, the product database 102, the patient database 106 and the linking database 124 are a same database 200. The database 200 comprises a product table 202, a patient table 204 and a linking table 206. In both the product table 202 and the patient table 204 there are various attribute fields, such as a product attribute field 208 and a patient attribute field 210, for respectively defining the product information 104 and the patient record 108. Moreover, in both the product table 202 and the patient table 204 there are a reference field, such as a product reference field 212 and a patient reference field 214, for respectively referencing the product information 104 and the patient record 108. Although the number and the type of attribute fields 208, 220 is variable, in one exemplary aspect, the product information 104 comprises the following attribute fields 208: product code, product serial number, product name, product purchase date, product expiry date, product supplier contact information and product manufacturer's number. In contrast, the patient record 108 comprises at least one of the following attribute fields 210: a patient number, an event number, patient hospital card number, patient medical insurance number, patient name, patient date of birth, patient sex, patient contact information, patient emergency contact information. Alternately, the product information 104 and the patient record 108 could include one or several of the listed attribute fields.

Further presented in FIG. 2 is the linking table 206 that comprises the product reference field 212 and the patient reference field 214. These reference fields together form the link 126 which corresponds to adding the referenced product information 104 to the referenced patient record 108. Thus, in the event of a product recall, where a particular product having a given serial number needs to be retraced, it is possible with the present system 100, to find the patient on whom the particular product was used or implanted.

Returning to FIG. 1, according to an aspect, the system 100 further comprises a user interface module 130 for allowing a user to retrieve data stored in at least one of the databases (102, 106 and 124). It is possible for the user to retrieve various types of data corresponding to either the product information 104, the patient record 108 or the link 126. According to one aspect, the user interface module 130 allows a user to retrieve "patient contact information" based on a "product serial number". With this user interface module 130, it is possible for the user to trace the patient(s) in which or on which a specific product has been used. According to another case, the user interface module 130 allows the user to retrieve a "product serial number" based on a "patient hospital card number". Furthermore, it is possible for the user to list the products that have been used in or on a specific patient. Depending on the various attribute fields that define either the product information 104 or the patient record 108, the user interface module 130 allows the user to perform correlations and extract corresponding resulting data.

Moreover, according to yet another aspect, the system 100 further comprises a reporting module 132. The reporting module 132 is adapted to produce a report according to data corresponding to either the product information 104, the patient record 108 or the link 126. The reporting module 132 is adapted to produce a report based on a request of the user through the user interface module 130. In one aspect the reporting module 132 is adapted to produce a report for tracking purposes. In another aspect the report module 132 is adapted to produce a report for managing the product expiry date. When an expired product is identified, the report module 132 is adapted to automatically send the report to a user or a supplier for having the expired product replaced.

Figure 3:
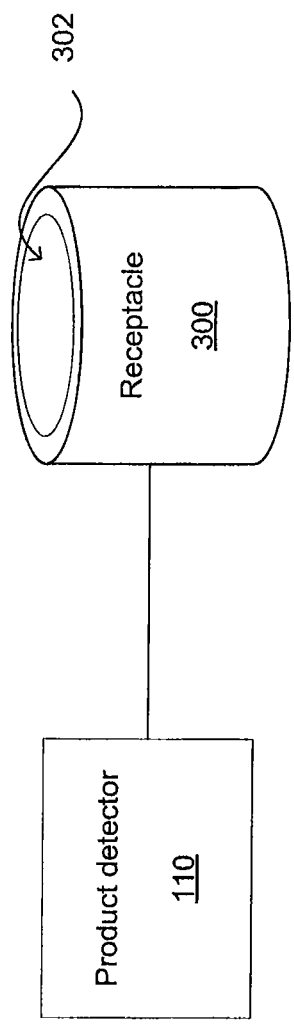
FIG. 3 is a block diagram of a product detector affixed to a receptacle according to an aspect of the system.

Presented in FIG. 3, the product detector 110 is affixed to a receptacle 300. In one aspect of the present invention, the receptacle 300 is a bin for containing product packages to be discarded. Once the product package is opened, and it's contained product is withdrawn from the product package for being used on or within a patient, the product package is thrown into the receptacle 300. According to one aspect, the product detector 110 is adapted to detect the product identifier 112 when the product package enters the receptacle 300. In this aspect, the product detector 110 is directed towards an opening 302 of the receptacle 300 and, as the product package passes through the opening 302, the product detector 110 is adapted to detect the product identifier 112 that is affixed to the product package. Furthermore, the receptacle 300 is adapted to meet hospital regulations in terms of infection control and safety issue.

According to another aspect, the product detector 110 is adapted to detect the product identifier 112 once the product package is within the receptacle 300. In this aspect, the product detector 110 is directed towards an inner side of the receptacle 300 and, once the product package is placed in the receptacle 300, the product detector 110 is adapted to detect the product identifier 112 that is affixed to the product package.

According to yet another aspect, the product detector 110 is adapted to generate the product identifier message 114 only once, after the product package is placed in the receptacle 300. In this aspect, the product detector 110 comprises a memory for storing a list of detected product identifiers. As the product identifier 112 is detected, the product detector 110 compares the product identifier 112 to the list, and if there is a match, the product detector 110 does not generate the product identifier message 114. However, if there is no match, the product detector 110 generates the product identification message 114 and then adds the product identifier 112 to the list. Consequently, this reduces the number of product identification messages 114 that are generated and liberates the adding module 122 from having to make the verification of whether there is duplication in the received product identifier messages 114.

Figure 4:
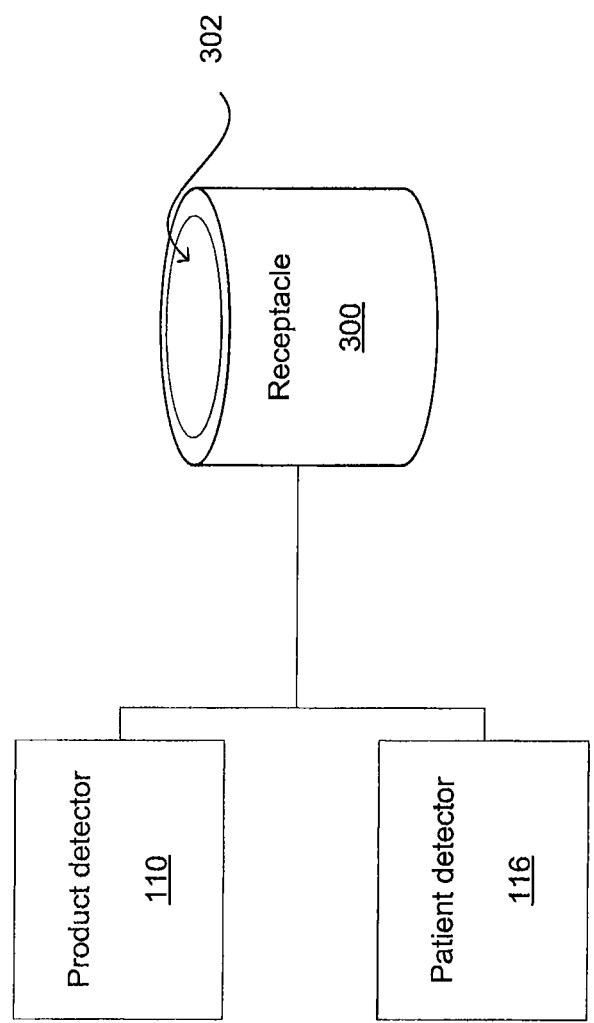
FIG. 4 is a block diagram of the product detector and a patient detector that are affixed to the receptacle according to an aspect of the system.

Presented in FIG. 4, both the product detector 110 and the patient detector 116 are affixed to the receptacle 300. In general, the receptacle 300 may be provided with wheels and be located for allowing easy access thereto, such as in proximity to where medical care is given. According to one aspect, the patient detector 116 is adapted to detect the patient identifier 118 when the patient or the patient identifier 118 becomes in proximity with the receptacle 300, such as for example when the patient enters a room where the receptacle 300 is located. The room may be any type of area that is enclosed, semi-enclosed or open. In one aspect, the room is a hospital room where medical care is normally given to the patient. In another aspect, the location is a mobile hospital bed where the patient is normally laid down for receiving medical care, etc. As the patient or the patient identifier 118 becomes in proximity with the patient detector 116, the patient identifier 118 is detected. Thereafter, when medical care is given to the patient and products are used on the patient, for each product used the product identifier 112 is detected, once the product package is thrown into the receptacle 300. The corresponding product information 104 is then added to the patient record 108 corresponding to the last detected patient identifier 118.

According to another aspect, the patient detector 116 is adapted to detect the patient identifier 118 when the patient identifier 118 has been in proximity therewith for a certain time. In this aspect, the patient detector 116 may be directed toward a specific location where the patient is usually placed for receiving care. Furthermore, the patient detector 116 may be adapted to generate the patient identifier message 120 only once, thus reducing the number of patient identification messages 120 generated and liberating the adding module 122 from having to make a verification of whether there is duplication in the received patient identifier messages 120. The patient detector 116 may also be a card that is brought in proximity or that is inserted into the receptacle 300. A keypad may also be used to enter the patient identifier 118 into the receptacle 300.

Figure 5:
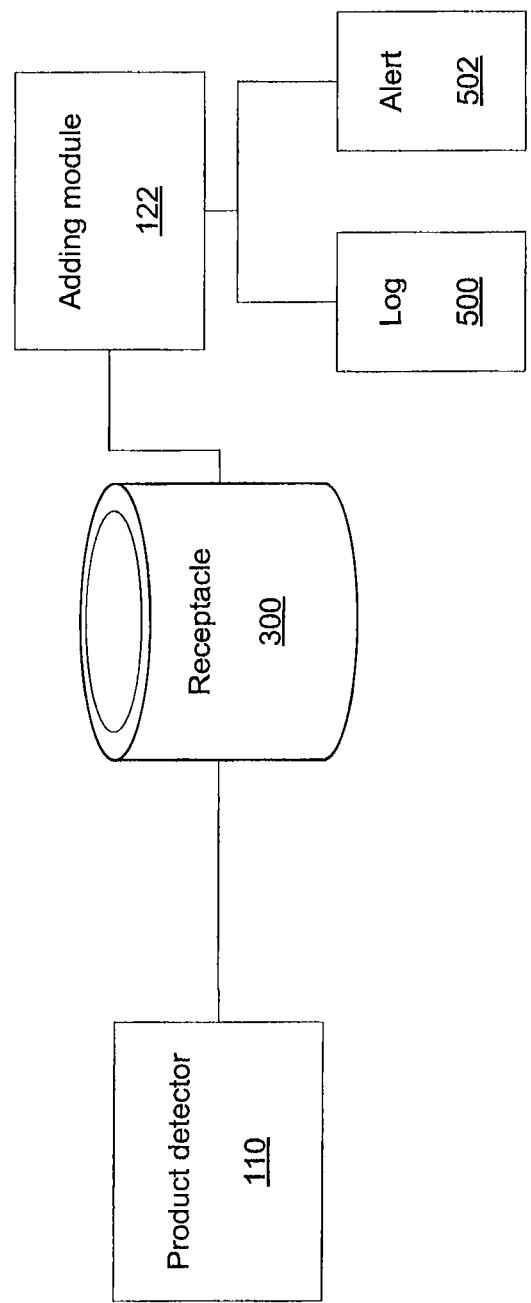
FIG. 5 is a block diagram of the product detector and an adding module affixed to the receptacle according to an aspect of the system.

Presented in FIG. 5, according to an aspect of the system 100, the product detector 110 is affixed to the receptacle 300 along with the adding module 122. This aspect may enable the addition of the product information 104 to the patient record 108 from the receptacle 300. Consequently, risk of loosing the product identifier message 114 is lowered. Also, the product identifier message 114 is timely received by the adding module 122 since there is no need for the message 114 to travel through a communication network for reaching the adding module 122. Furthermore, it makes it possible for a user to instantaneously track the products that have been used on the patient.

According to another aspect, a logging module 500 is connected to the adding module 122. Once the product information 104 is added to the patient record 108, the adding module 122 generates a description of the addition process. To do so, the adding module 122 queries the database that holds the product attribute fields 208 and the patient attribute fields 210, and from this, the adding module 122 generates the description of the addition process. The logging module 500 then uses the description of the addition process and produces a log. The description of the addition process may comprise one or several of the following attributes: a patient hospital card number, a patient name, a product serial number, a product name, a product expiry date and a time and date at which the addition process took place.

According to yet another aspect, an alert module 502 may be connected to the adding module 122. Before adding the product information 104 to the patient record 108, the adding module 122 verifies if there are any existent errors that may render the addition process impossible or undesirable. When there exists an error or a counter indication, the adding module 122 generates an error message and the alert module 502 then produces an alert for informing the medical personal of the error or counter indication. Various causes of error are possible such as a product expiry date.

Figure 6:
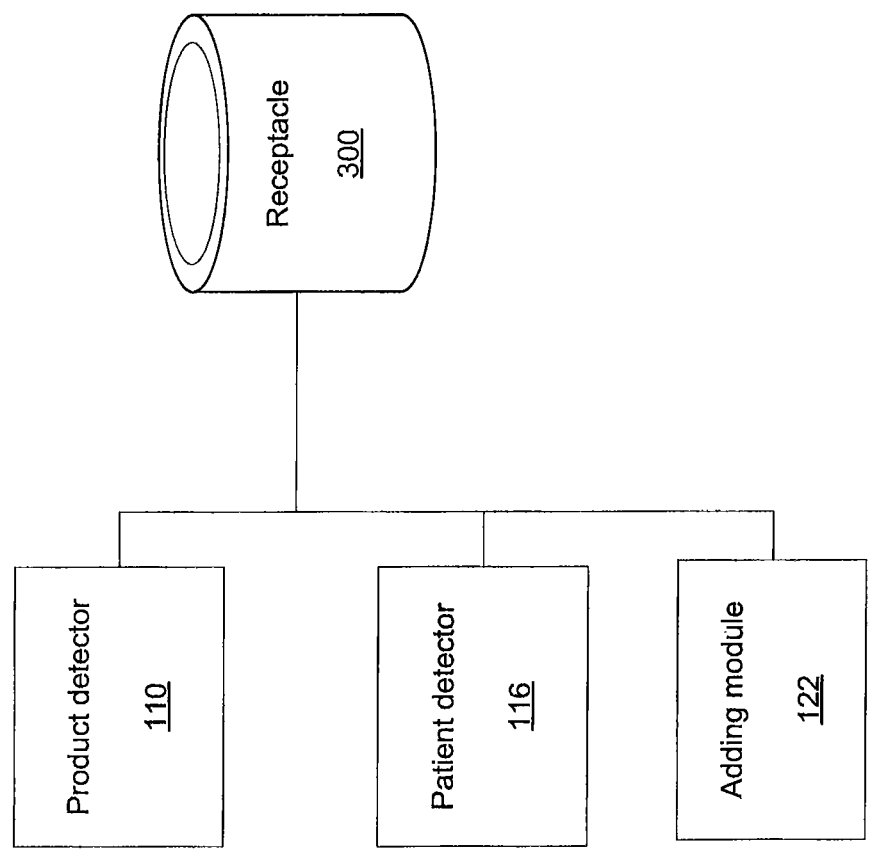
FIG. 6 is a block diagram of the product detector, the patient detector and the adding module affixed to the receptacle according to an aspect of the system.

Presented in FIG. 6, according to an aspect of the system 100, the product detector 110, the patient detector 116 and the adding module 122 are all affixed to the receptacle 300, and are in direct connection there between. In this particular aspect, the addition process of the product information 104 to the patient record 108 takes place at the receptacle 300. As both the product detector 110 and the patient detector 116 are affixed to the receptacle 300, the risk of loosing either of the product identifier message 114 or the patient identifier message 120 before the adding module 122 receives the messages 114, 120 is lower.

A skilled reader will recognize that it is possible for the databases (102, 106, 124, 200), the product detector 110, the patient detector 116 or the adding module 122 to either be independently connected, connected to one another or to be connected to any other part of the system 100 without affecting the workings of this system 100. The connection there between may be done through a wired or a wireless network, may be direct or indirect. The product detector 110 and the patient detector 116 thus generate respectively the product identifier message 114 and the patient identifier message 120 and send the product identifier message 114 and the patient identifier message 120 to the adding module 122 which is either co-located, or separate there from. Any type of communication means and standards may be used to perform the sending of the patient identifier message 120 and product identifier message 114 to the adding module 122.

Figure 7:
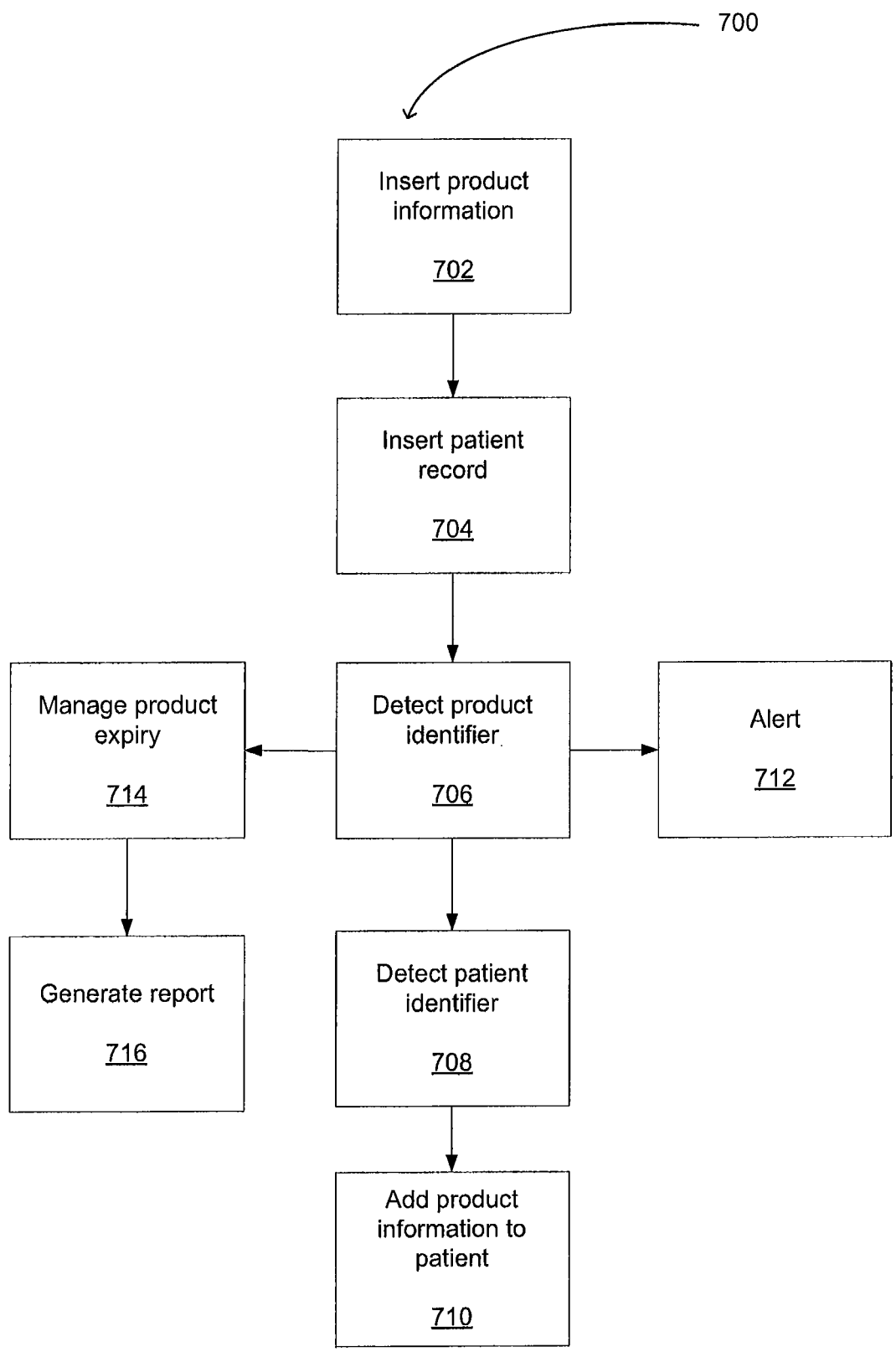
FIG. 7 is a flow diagram of a method for adding product information to a patient record.

Presented in FIG. 7 is a method 700 for adding product information to a patient record. The method 700 comprises inserting 702 into the product database 102 the product information 104, and inserting 704 into the patient database 106 the patient record 108. Moreover, the method 700 comprises detecting 706 the product identifier 112 corresponding to the product information 104, and detecting 708 the patient identifier 118 corresponding to the patient record 108. Also, the method 700 comprises adding 710 the product information 104 to the patient record 108. According to one aspect, the method 700 further comprises alerting 712 a user when an incompatibility is detected with the product information 104. According to another aspect, the method 700 further comprises managing 714 a product expiry date for identifying an expired product and generating 716 a report for notifying the user or the supplier that the identified expired product must be replaced.

While the present system 100 and method 700 have been shown and described with reference to different aspects thereof, it will be recognized by those skilled in the art that various changes in form and detail may be made herein without departing from the spirit and scope of the invention as defined by the appended claims.

The invention claimed is:

1. A system for automatically tracking products used for medical treatment, the system comprising:
   a product database for storing at least one product information corresponding to at least one product, each product contained within a product package;
   a patient database for storing a patient record corresponding to a patient;
   a package discard receptacle adapted for receiving the product package to be discarded after the contained product has been withdrawn from that product package;
   a product package detector affixed to the package discard receptacle adapted to receive radio frequency signals from inside the package discard receptacle, the product package detector:
      detecting a radio frequency product package identifier affixed to the product package once the product package is placed inside the package discard receptacle, the radio frequency product package identifier corresponding to the product information, and
      automatically generating a product identifier message in response to detection of the radio frequency product package identifier on the product package, the product package identifier message indicative that the product package has been discarded and that the corresponding product has been consumed;
   a patient detector affixed to the package discard receptacle, the patient detector for automatically detecting a patient identifier corresponding to the patient record and generating a patient identifier message when the patient is within a predetermined distance from the package discard receptacle; and
   an adding module for adding the product information to the patient record based on receiving the patient identifier message and the product identifier message.

2. The system of claim 1 wherein the adding module is affixed to the receptacle.

3. The system of claim 2 wherein the adding module is adapted to add in the patient record a pointer to the product information in the product database.

4. The system of claim 2 wherein the adding module is adapted to store in a linking database a link corresponding to the product information and the patient record.

5. The system of claim 4 wherein the linking database is the patient database.

6. The system of claim 4 wherein the linking database is the product database.

7. The system of claim 1 wherein the patient database and the product database form one single database.

8. The system of claim 1 wherein the product information comprises at least one of the following: a product code, a product serial number, a product name, a product purchase date, a product expiry date, a product supplier contact information, and a product manufacturer's number.

9. The system of claim 1 wherein the patient record comprises at least one of the following: a patient number, an event number, a patient hospital card number, a patient medical insurance number, a patient name, a patient date of birth, a patient sex, a patient contact information, and a patient emergency contact information.

10. A method for automatically tracking products used for medical treatment, the method comprising:
   inserting into a product database the at least one product information corresponding to at least one product, each contained within a product package;
   inserting into a patient database a patient record corresponding to a patient;
   receiving in a package discard receptacle the product package to be discarded after the contained product has been withdrawn from the product package;
   detecting, using a product package detector affixed to the package discard receptacle and adapted to receive radio frequency signals from inside the package discard receptacle, a radio frequency product package identifier affixed to the product package once the product package is placed inside the package discard receptacle, the radio frequency product package identifier corresponding to the product information;
   automatically generating a product identifier message in response to detection of the radio frequency product package identifier on the product package the product package identifier message indicative that the product package has been discarded and that the corresponding product has been consumed;
   automatically detecting a patient identifier corresponding to the patient record and generating a patent identifier message using a patient detector affixed to the package discard receptacle when the patient is within a predetermined distance from the package discard receptacle; and upon receipt of the product identifier message and the patient identifier message, adding the product information to the patient record.

11. The method of claim 10 further comprising alerting a user when an incompatibility is detected between the product and the patient record.

12. The method of claim 10 further comprising managing a product expiry date for identifying an expired product.

13. The method of claim 12 further comprising generating a report to a user for replacing the identified expired product.

14. A system for automatically tracking products used for medical treatment, the system comprising:
 a product database for storing at least one product information corresponding to at least one product, each product contained within a product package;
 a patient database for storing a patient record;
 a package discard receptacle adapted for receiving the product package to be discarded after the contained product has been withdrawn from that product package;
 a product package detector adapted to receive radio frequency signals from inside the package discard receptacle, the product package detector:
  detecting a radio frequency product package identifier affixed to the product package once the product package is placed inside the package discard receptacle, the radio frequency product package identifier corresponding to the product information, and
  automatically generating a product identifier message in response to detection of the radio frequency product package identifier on the product package, the product package identifier message indicative that the product package has been discarded;
 an adding module for adding the product information to the patient record based on receiving the product identifier message.

15. A method for automatically tracking products used for medical treatment, the method comprising:
 inserting into a product database the at least one product information corresponding to at least one product, each contained within a product package;
 inserting into a patient database a patient record;
 receiving in a package discard receptacle the product package to be discarded after the contained product has been withdrawn from the product package;
 detecting, using a product package detector adapted to receive radio frequency signals from inside the package discard receptacle, a radio frequency product package identifier affixed to the product package once the product package is placed inside the package discard receptacle, the radio frequency product package identifier corresponding to the product information;
 automatically generating a product identifier message in response to detection of the radio frequency product package identifier on the product package the product package identifier message indicative that the product package has been discarded; and
 upon receipt of the product identifier message, adding the product information to the patient record.

* * * * *